United States Patent [19]
Olson

[11] Patent Number: 4,912,056
[45] Date of Patent: * Mar. 27, 1990

[54] TREATMENT OF DENIM WITH CELLULASE TO PRODUCE A STONE WASHED APPEARANCE

[75] Inventor: Lynne A. Olson, Mendota Heights, Minn.

[73] Assignee: Ecolab Inc., St. Paul, Minn.

[ * ] Notice: The portion of the term of this patent subsequent to May 23, 2006 has been disclaimed.

[21] Appl. No.: 283,563

[22] Filed: Dec. 8, 1988

Related U.S. Application Data

[62] Division of Ser. No. 96,953, Sep. 15, 1987, Pat. No. 4,832,864.

[51] Int. Cl.[4] .................... D06M 16/00; C12N 9/96; C12N 9/42

[52] U.S. Cl. .................................... 435/263; 8/116.1; 252/174.12; 252/DIG. 12; 435/188; 435/209; 435/264

[58] Field of Search ............... 435/188, 209, 263, 264; 252/174.12, DIG. 12; 8/102, 116.1

[56] References Cited

U.S. PATENT DOCUMENTS

| | | | |
|---|---|---|---|
| 4,381,247 | 4/1983 | Nakagawa et al. | 252/95 |
| 4,388,077 | 6/1983 | Ruck | 8/138 |
| 4,435,307 | 3/1984 | Barbesgaard et al. | 252/174.12 |
| 4,443,355 | 4/1984 | Murata et al. | 252/174.12 |
| 4,479,881 | 10/1984 | Tai | 252/8.8 |
| 4,661,289 | 4/1987 | Parslow et al. | 252/547 |
| 4,740,213 | 4/1988 | Ricci | 8/108 |

FOREIGN PATENT DOCUMENTS

| | | |
|---|---|---|
| 177165 | 4/1986 | European Pat. Off. . |
| 220016 | 4/1987 | European Pat. Off. . |
| 252317 | 1/1988 | European Pat. Off. . |
| 2136029 | of 0000 | United Kingdom . |
| 1368599 | 2/1974 | United Kingdom . |
| 2094826 | 9/1982 | United Kingdom . |
| 2095275 | 9/1982 | United Kingdom . |

OTHER PUBLICATIONS

Celluzyme TM Novo Enzymes Product Sheet, Apr., 1987.
Merck Index, p. 210, 8th edition, 1968.
Wall Street Journal, May 29, 1987, pp. 1, 9.

*Primary Examiner*—David M. Naff
*Attorney, Agent, or Firm*—Merchant, Gould, Smith, Edell, Welter & Schmidt

[57] ABSTRACT

Denim having a stone washed appearance is produced without stones by treating with a cellulase enzyme. Unsewn dyed denim fabric or a newly manufactured garment made of dyed denim fabric is contacted with an aqueous composition containing at least about 2500 CMCS units of cellulase per liter, and subjected to mechanical action. Preferably, the aqueous composition provides at least about 6000 CMC units of cellulase per pound of unsewn fabric or garment. The aqueous may also contain an electrolyte, a buffer, a builder salt a cellulase activator, an antioxidant and a solubilizer.

18 Claims, 1 Drawing Sheet

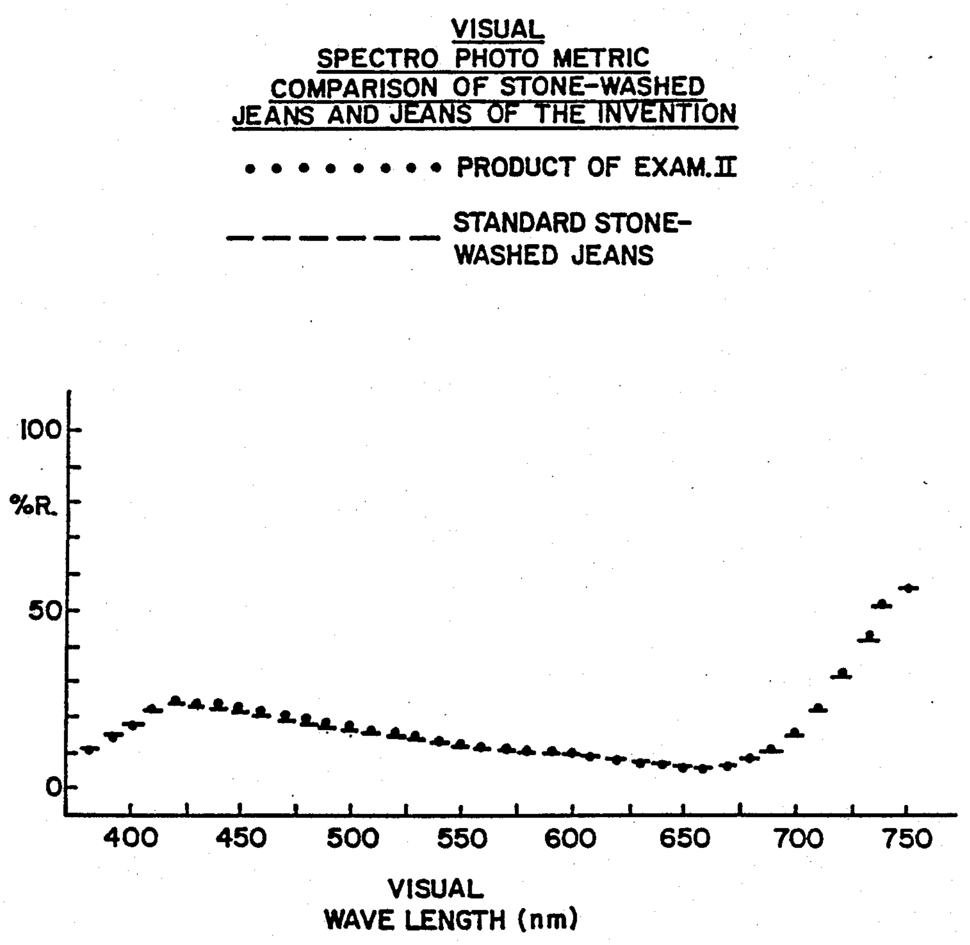
VISUAL
SPECTRO PHOTO METRIC
COMPARISON OF STONE-WASHED
JEANS AND JEANS OF THE INVENTION
PRODUCT OF EXAM. II
STANDARD STONE-WASHED JEANS
100
%R.
50
0
400
450
500
550
600
650
700
750
VISUAL
WAVE LENGTH (nm)

TREATMENT OF DENIM WITH CELLULASE TO PRODUCE A STONE WASHED APPEARANCE

This is a division of application Ser. No. 07/096,953, filed Sept. 15, 1987, now U.S. Pat. No. 4,832,864.

FIELD OF THE INVENTION

The invention relates to the manufacture of clothing from dyed cellulosic fabrics. More particularly, the invention relates to pumice-free compositions and processes used in the manufacture of a clothing item, preferably from denim fabric dyed with indigo, that can produce in a clothing item a distressed, "used and abused" appearance that is virtually indistinguishable from the appearance of "stone washed" clothing items made by traditional pumice processing.

BACKGROUND OF THE INVENTION

Clothing made from cellulosic fabrics such as cotton and in particular indigo dyed denim fabrics have been common items of clothing for many years. Such clothing items are typically sold after they are sewn from sized and cut cloth. Such clothes and particularly denim clothing items are stiff in texture due to the presence of sizing compositions used to ease manufacturing, handling and assembling of the clothing items and typically have a fresh dark dyed appearance. After a period of wear, the clothing items, particularly denim, can develop in the clothing panels and on seams, localized areas of variations, in the form of a lightening, in the depth or density of color. In addition a general fading of the clothes can often appear in conjunction with the production of a "fuzzy" surface, some pucker in seams and some wrinkling in the fabric panels. Additionally, after laundering, sizing is substantially removed from the fabric resulting in a softer feel. In recent years such a distressed or "used and abused" look has become very desirable, particularly in denim clothing, to a substantial proportion of the public. To some extent, a limited pre-worn appearance, which has a uniform color density different than the variable color density in the typical stone-washed item, can be produced through prewashing or preshrinking processes.

The preferred methods for producing the distressed "used and abused" look involve stone washing of a clothing item. Stone washing comprises contacting a denim clothing item or items in large tub equipment with pumice stones having a particle size of about 1 to 10 inches and with smaller pumice particles generated by the abrasive nature of the process. Typically the clothing item is tumbled with the pumice while wet for a sufficient period such that the pumice abrades the fabric to produce in the fabric panels, localized abraded areas of lighter color and similar lightened areas in the seams. Additionally the pumice softens the fabric and produces a fuzzy surface similar to that produced by the extended wear of the fabric.

The 1 to 10 inch pumice stones and particulate pumice abrasion by-products can cause significant processing and equipment problems. Particulate pumice must manually be removed from processed clothing items (de-rocking) because they tend to accumulate in pockets, on interior surfaces, in creases and in folds. In the stone washing machine, the stones can cause overload damage to electric motors, mechanical damage to transport mechanisms and washing drums and can significantly increase the requirements for machine maintenance. The pumice stones and particulate material can clog machine drainage passages and can clog drains and sewer lines at the machine site. Further, the abraded pumice can clog municipal sewer lines, can damage sewage processing equipment, and can significantly increase maintenance required in municipal sewage treatment plants. These problems can add significantly to the cost of doing business and to the purchase price of the goods.

In view of the problems of pumice in stone washing, increasing attention has been directed to finding a replacement for stone washing in garment manufacture (see the Wall Street Journal, May 9, 1987, p. 1.). One avenue of investigation involves using a replacement stone such as a synthetic abrasive. In particular, ceramic balls such as those used in ball mills and irregular hard rubber pieces, which can be used without producing abraded by-products, have been experimented with in stone washing processes. These materials reduce the unwanted effects caused by particulate by-product pumice but do not significantly reduce machine damage caused by stones or the required maintenance on stone-containing laundry tubs. As a result, significant attention has been directed to producing a stone-free or pumice-free "stone washed" process that can produce a stone-washed denim look.

One disadvantage in pumice processing is that pumice cannot be used in tunnel washers, the largest commercial washing machines. Pumice cannot be circulated through the tunnel machines due to machine internal geometry. The use of larger-scale tunnel washers could significantly increase the productivity of the processes with the use of a stone or pumice-free composition that produces a genuine "stone-washed" look.

Barbesgarrd et al, U.S. Pat. No. 4,435,307 teach a specific cellulase enzyme that can be obtained from Humicola insolens which can be used in soil removing detergent compositions. Martin et al, European patent application Ser. No. 177,165 teach fabric washing compositions containing a surfactant, builders, and bleaches in combination with a cellulase composition and a clay, particularly a smectite clay. Murata et al, U.K. patent application Ser. No. 2,095,275 teach enzyme containing detergent compositions comprising an alkali cellulase and typical detergent compositions in a fully formulated laundry preparation. Tai, U.S. Pat. No. 4,479,881 teaches an improved laundry detergent containing a cellulase enzyme in combination with a tertiary amine in a laundry preparation. Murata et al, U.S. Pat. No. 4,443,355 teach laundry compositions containing a cellulase from a cellulosmonas bacteria. Parslow et al, U.S. Pat. No. 4,661,289 teaches fabric washing and softening compositions containing a cationic softening agent and a fungal cellulase in conjunction with other typical laundry ingredients. Suzuki, U.K. patent application Ser. No. 2,094,826 teaches detergent laundry compositions containing a cellulase enzyme.

Dyed cellulosic clothing (such as denim) have been treated with desizing enzymes, detergents, bleaches, sours and softeners in prewashing and preshrinking processes. These variations are not intended to and do not duplicate the "stone-washed " look. A stone or pumice-free "stone-washed" process that produces the true stone-washed look has yet to be developed.

BRIEF DESCRIPTION OF THE INVENTION

We have found that the "stone washed" appearance that takes the form of variations in local color density in fabric panels and seams of dyed cellulosic fabric, particularly in denim, clothing items can be substantially obtained using a stone or pumice-free process in which the clothing items are mechanically agitated in a tub with an aqueous composition containing amounts of a cellulase enzyme that can degrade the cellulosic fabric and can release the fabric dye or dyes.

The aqueous treatment compositions are obtained by diluting a novel "stone-wash" liquid or solid concentrate consisting essentially of a cellulase enzyme and a diluent such as a compatible surfactant composition, a non-aqueous solvent or a solid-forming agent capable of suspending the cellulase without significant loss of enzymatic activity.

The use of cellulase enzyme preparations is known in laundry cleaning or detergent compositions. Such detergent compositions that are designed for soil removal typically contain surfactants (typically anionic), fillers, brighteners, clays, cellulase and other enzymes (typically proteases, lipases or amylases) and other laundry components to provide a full functioning laundry detergent preparation. The cellulase enzymes in such laundry preparations are typically used (at a concentration less than 500 to 900 CMC units per liter of wash liquor) for the purpose of removing surface fibrils or particles produced by fabric wear which tend to give the fabric a used or faded appearance. The cellulase enzymes in combination with the surfactants used in common laundry compositions for cleaning apparently can remove particulate soil and can restore the new appearance of clothing items. Such compositions are not known to introduce, into clothing, areas of variation in color density which can generally be undesirable in the laundry processing.

For the purpose of this invention, the terms stone-washed appearance and variations in local color depth or density in fabric materials are synonymous. The stone-washed appearance is produced in standard processing in fabric through an abrasion process wherein pumice apparently removes surface bound dye in a relatively small portion of the surface of a garment. Such an abraded area varies from the surrounding color or depth density and is substantially lighter in color. The production of such relatively small local areas of lightness or variation in color depth or density is the goal of both pumice containing stone washing processes in the prior art and Applicant's stone-free chemical treatment methods and compositions.

BRIEF DESCRIPTION OF DRAWINGS

FIG. 1 is a graph demonstrating the similarity in visual spectrophotometric character of authentic stone-washed jeans when compared to jeans produced by the compositions and methods of the invention.

DETAILED DESCRIPTION OF THE INVENTION

The stone-free "stone washed" methods of the invention involve contacting clothing items or denim fabric with an aqueous solution containing a cellulase enzyme composition and agitating the treated fabric for a sufficient period of time to produce localized variations in color density in the fabric. The fabric items can be wet by the solution and agitated apart from the bulk aqueous liquors or can be agitated in the liquor. Typically the aqueous solution contains the cellulase enzyme and a cellulase compatible surfactant that increases the wetting properties of the aqueous solution to enhance the cellulase effect.

The aqueous treatment solutions are typically prepared from a liquid or solid concentrate composition which can be diluted with water at appropriate dilution ratios to formulate the aqueous treatment. The "stone wash concentrate" compositions typically contain the cellulase enzyme and a diluent such as a compatible surfactant, a non-aqueous solvent or a solid-forming agent that can produce in a treatment liquor a suspension of the cellulase enzyme without significant enzyme activity loss.

The solid concentrate compositions typically comprise a suspension of the cellulase enzyme composition in a solid matrix. The solid matrices can be inorganic or organic in nature. The solid concentrates can take the form of large masses of solid concentrate or can take the form of granular or pelletized composition. The solid concentrates can be used in commercial processes by placing the solid concentrate materials in dispensers that can direct a dissolving spray of water onto the solid or pellet material thereby creating a concentrated solution of the material in water which is then directed by the dispenser into the wash liquors contained in the commercial drum machines.

CELLULASE ENZYME

Enzymes are a group of proteins which catalyze a variety of typically biochemical reactions. Enzyme preparations have been obtained from natural sources and have been adapted for a variety of chemical applications. Enzymes are typically classified based on the substrate target of the enzymatic action. The enzymes useful in the compositions of this invention involve cellulase enzymes (classified as I.U.B. No. 3.2.1.4., EC numbering 1978). Cellulase are enzymes that degrade cellulose by attacking the C(1→4) (typically beta) glucosidic linkages between repeating units of glucose moieties in polymeric cellulosic materials. The substrate for cellulase is cellulose, and cellulose derivatives, which is a high molecular weight natural polymer made of polymerized glucose. Cellulose is the major structural polymer of plant organisms. Additionally cellulose is the major structural component of a number of fibers used to produce fabrics including cotton, linen, jute, rayon and ramie, and others.

Cellulases are typically produced from bacterial and fungal sources which use cellulase in the degradation of cellulose to obtain an energy source or to obtain a source of structure during their life cycle. Examples of bacteria and fungi which produce cellulase are as follows: *Bacillus hydrolyticus, Cellulobacillus mucosus, cellulobacillus myxogenes, Cellulomonas sp., Cellvibrio fulvus, Celluvibrio vulgaris, Clostridium thermocellulaseum, Clostridium thermocellum, Corynebacterium sp., Cytophaga globulosa, Pseudomonas fluoroescens var. cellulosa, Pseudomonas solanacearum, Bacterioides succinogenes, Ruminococcus albus, Ruminococcus flavefaciens, Sorandium composition, Butyrivibrio, Clostridium sp., Xanthomonas cyamopsidis, Sclerotium bataticola, Bacillus sp., Thermoactinomyces sp., Actinobifida sp., Actinomycetes sp., Streptomyces sp., Arthrobotrys superba, Aspergillus aureus, Aspergillus flavipes, Aspergillus flavus, Aspergillus fumigatus, Aspergillus fuchuenis, Aspergillus nidulans, Aspergillus niger, Aspergillus oryzae, Aspergillus rugulosus, Aspergillus sojae, Aspergillus sydwi, Aspergillus tamaril, Aspergillus terreus, Aspergillus unguis, Aspergillus ustus, Takamine-Cellulase, Aspergillus saitoi, Botrytis*

*cinerea, Botryodipiodia theobromae, Cladosporium cucummerinum, Cladosporium herbarum, Coccospora agricola, Curvuiaria lunata, Chaetomium thermophile var. coprophile, Chaetomium thermophile var. dissitum, Sporotrichum thermophile, Taromyces amersonii, Thermoascus aurantiacus, Humicola grisea var. thermoidea, Humicola insolens, Malbranchea puichella var. sulfurea, Myriococcum albomyces, Stilbella thermophile, Torula thermophila, Chaetomium globosum, Dictyosteiium discoideum, Fusarium sp., Fasarium bulbigenum, Fusarium equiseti, Fusarium lateritium, Fusarium lini, Fusarium oxysporum, Fusarium vasinfectum, Fusarium dimerum, Fusarium japonicum, Fusarium scirpi, Fusarium solani, Fusarium moniliforme, Fusarium roseum, Helminthosporium sp., Memnoniella echinata, Humicola fucoatra, Humicola grisea, Monilia sitophila, Monotospora brevis, Mucor pusillus, Mycosphaerella citrulina, Myrothecium verrcaria, Papulaspore sp., Penicillium sp., Penicillium capsulatum, Penicillium chrysogenum, Penicillium, frequentana, Penicillium funicilosum, Penicillium janthinellum, Penicillium luteum, Penicillium piscarium, Penicillium soppi, Penicillium spinulosum, Penicillium turbaturn, Penicillium digitatum, Penicillium expansum, Penicillium pusitlum, Penicillium rubrum, Penicillium wortmanii, Penicillium variabile, Pestalotia palmarum, Pestalotiopsis westerdijkii, Phoma sp., Schizophyllum commune, Scopulariopsis brevicaulis, Rhizopus sp., Sporotricum carnis, Sporotricum pruinosum, Stachybotrys atra, Torula sp., Trichoderma viride (reesei), Trichurus cylindricus, Verticillium albo atrum, Aspergillus cellulosae, Penicillium glaucum, Cunninghamella sp., Mucor mucedo, Rhyzopus chinensis, Coremiella sp., Karlingia rosea, Phytophthora cactorum, Phytophthora citricola, Phytophtora parasitica, Pythium sp., Saprolegniaceae, Ceratocystis ulmi, Chaetomium globosum, Chaetomium indicum, Neurospora crassa, Sclerotium rolfsii, Aspergillus sp., Chrysosporium lignorum, Penicillium notatum, Pyricularia oryzae, Collybia veltipes, Coprinus sclerotigenus, Hydnum henningsii, Irpex lacteus, Polyporus sulphreus, Polyporus betreus, Polystictus hirfutus, Trametes vitata, Irpex consolus, Lentines lepideus, Poria vaporaria, Fomes pinicola, Lenzites styracina, Merulius lacrimans, Polyporus palstris, Polyporus annosus, Polyporus versicolor, Polystictus sanguineus, Poris vailantii, Puccinia graminis, Tricholome fumosum, Tricholome nudum, Trametes sanguinea,* Polyporus schweinitzil FR., *Conidiophora carebella,* Cellulase AP (Amano Pharmaceutical Co., Ltd.), Cellulosin AP (Ueda Chemical Co., Ltd.), Cellulosin AC (Ueda Chemical Co., Ltd.), Cellulase-Onozuka (Kinki Yakult Seizo Co., Ltd.), Pancellase (Kinki Yakult Seizo Co., Ltd.), Macerozyme (Kinki Yakult Seizo Co., Ltd.), Meicelase (Meiji Selka Kaisha, Ltd.), Celluzyme (Nagase Co., Ltd.), Soluble sclase (Sankyo Co., Ltd.), Sanzyme (Sankyo Co., Ltd.), Cellulase A-12-C (Takeda Chemical Industries, Ltd.), Toyo-Cellulase (Toyo Jozo Co., Ltd.), Driserase (Kyowa Hakko Kogyo Co., Ltd.), Luizyme (Luipold Werk), Takamine-Cellulase (Chemische Fabrik), Wallerstein-Cellulase (Sigma Chemicals), Cellulase Type I (Sigma Chemicals), Cellulase Serva (Serva Laboratory), Cellulase 36 (Rohm and Haas), Miles Cellulase 4,000 (Miles), R & H Cellulase 35, 36, 38 conc (Phillip Morris), Combizym (Nysco Laboratory), Cellulase (Makor Chemicals), Celluclast, Celluzyme, Cellucrust (NOVO Industry), and Cellulase (Gist-Brocades). Cellulase preparations are available from Accurate Chemical & Scientific Corp., Alltech, Inc., Amano International Enzyme, Boehringer Mannheim Corp., Calbiochem Biochems, Carolina Biol. Supply Co., Chem. Dynamics Corp., Enzyme Development, Div. Biddle Sawyer, Fluka Chem. Corp., Miles Laboratories, Inc., Novo Industrials (Biolabs), Plenum Diagnostics, Sigma Chem. Co., Un. States Biochem. Corp., and Weinstein Nutritional Products, Inc.

Cellulase, like many enzyme preparations, is typically produced in an impure state and often is manufactured on a support. The solid cellulase particulate product is provided with information indicating the number of international enzyme units present per each gram of material. The activity of the solid material is used to formulate the treatment compositions of this invention. Typically the commercial preparations contain from about 1,000 to 6,000 CMC enzyme units per gram of product.

SURFACTANT

A surfactant can be included in the treatment compositions of the invention. The surfactant can increase the wettability of the aqueous solution promoting the activity of the cellulase enzyme in the fabric. The surfactant increases the wettability of the enzyme and fabric. The surfactant facilitates the exclusion of air bubbles from fabric surfaces and the enzyme preparation, and promotes contact between enzyme and fabric surface. The properties of surfactants are derived from the presence of different functional groups.

Surfactants are classified and well known categories including nonionic, anionic, cationic and amphoteric surfactants.

Nonionic surfactants are surfactants having no charge when dissolved or dispersed in aqueous medium. The hydrophilic tendency of nonionic surfactants is derived from oxygen typically in ether bonds which are hydrated by hydrogen bonding to water molecules. Hydrophilic moieties in nonionics can also include hydroxyl groups and ester and amide linkages. Typical nonionic surfactants include alkyl phenol alkoxylates, aliphatic alcohol alkoxylates, carboxylic acid esters, carboxylic acid amides, polyalkylene oxide heteric and block copolymers, and others.

Nonionic surfactants are generally preferred for use in the compositions of this invention since they provide the desired wetting action and do not degrade the enzyme activity. Preferred nonionic surfactants include polymeric molecules derived from repeating units of ethylene oxide, propylene oxide, or mixtures thereof. Such nonionic surfactants include both homopolymeric, heteropolymeric, and block polymeric surfactant molecules. Included within the preferred class of nonionic surfactants are polyethylene oxide polymers, polypropylene oxide polymers, ethylene oxide-propylene oxide block copolymers, ethoxylated $C_{1-18}$ alkyl phenols, ethoxylated $C_{1-18}$ aliphatic alcohols, pluronic surfactants, reverse pluronic surfactants, and others.

Particularly preferred nonionics include: polyoxyethylene alkyl or alkenyl ethers having alkyl or alkenyl groups of a 10 to 20 average carbon number and having 1 to 20 moles of ethylene oxide added; polyoxyethylene alkyl phenyl ethers having alkyl groups of a 6 to 12 average carbon number and having 1 to 20 moles of ethylene oxide added; polyoxypropylene alkyl or alkenyl ethers having alkyl groups or alkenyl groups of a 10 to 20 average carbon number and having 1 to 20 moles of propylene oxide added; polyoxybutylene alkyl or alkenyl ethers having alkyl groups of alkenyl groups of a 10 to 20 average carbon number and having 1 to 20 moles of butylene oxide added; nonionic surfactants having alkyl groups or alkenyl groups of a 10 to 20 average carbon number and having 1 to 30 moles in total of ethylene oxide and propylene oxide or ethylene oxide and butylene oxide added (the molar ratio of ethylene oxide to propylene oxide or butylene oxide being 0.1/9.9 to 9.9/0.1); or higher fatty acid alkanolamides or alkylene oxide adducts thereof. Less preferred surfactants include anionic, cationic and amphoteric surfactants.

Anionic surfactants are surfactants having a hydrophilic moiety in an anionic or negatively charged state in aqueous solution. Commonly available anionic surfactants include carboxylic acids, sulfonic acids, sulfuric acid esters, phosphate esters, and salts thereof.

Cationic surfactants are hydrophilic moieties wherein the charge is cationic or positive when dissolved in aqueous medium. Cationic surfactants are typically found in amine compounds, oxygen containing amines, amide compositions, and quaternary amine salts. Typical examples of these classes are primary and secondary amines, amine oxides, alkoxylated or propoxylated amines, carboxylic acid amides, alkyl benzyl dimethyl ammonium halide salts and others.

Amphoteric surfactants which contain both acidic and basic hydrophilic structures tend to be of reduced utility in most fabric treating processes.

SOLVENTS

Solvents that can be used in the liquid concentrate compositions of the invention are liquid products that can be used for dissolving or dispersing the enzyme and surfactant compositions of the invention. Because of the character of the preferred nonionic surfactants, the preferred solvents are oxygen containing solvents such as alcohols, esters, glycol, glycol ethers, etc. Alcohols that can be used in the composition of the invention include methanol, ethanol, isopropanol, tertiary butanol, etc. Esters that can be used include amyl acetate, butyl acetate, ethyl acetate, esters of glycols, and others. Glycols and glycol ethers that are useful as solvents in the invention include ethylene glycol, propylene glycol, and oligomers and higher polymers of ethylene or propylene glycol in the form of polyethylene or polypropylene glycols. In liquid concentrates the low molecular weight oligomers are preferred. In solid organic concentrates the high molecular weight polymers are preferred.

SOLID FORMING AGENTS

The compositions of the invention can be formulated in a solid form such as a cast solid, large granules or pellets. Such solid forms are typically made by combining the cellulase enzyme with a solidification agent and forming the combined material in a solid form. Both organic and inorganic solidification agents can be used. The solidification agents must be water soluble or dispersible, compatible with the cellulase enzyme, and easily used in manufacturing equipment.

Inorganic solid forming agents that can be used are typically hydratable alkali metal or alkaline earth metal inorganic salts that can solidify through hydration. Such compositions include sodium, potassium or calcium, carbonate, bicarbonate, tripolyphosphate silicate, and other hydratable salts. The organic solidification agents typically include water soluble organic polymers such as polyethylene oxide or polypropylene oxide polymers having a molecular weight of greater than about 1,000, preferably greater than about 1,400. Other water soluble polymers can be used including polyvinyl alcohol, polyvinyl pyrrolidone, polyalkyl oxazolines, etc. The preferred solidification agent comprises a polymer of polyethylene oxide having an average molecular weight of greater than about 1,000 to about 20,000, preferably 1,200 to 10,000. Such compositions are commercially available as CARBOWAX® 1540, 4000, 6000. To the extent that the nonionic surfactants and other ingredients are soluble in solid polymer compositions, the solid organic matrices can be considered solvent.

Additionally, the solid pellet-like compositions of the invention can be made by pelletizing the enzyme using well known pressure pelletizing techniques in which the cellulase enzyme in combination with a binder is compacted under pressure to a tablet or pellet composition.

ALKALIS OR INORGANIC ELECTROLYTES

The composition may also contain 1–50 wt-%, preferably 5–30 wt-% of one or more alkali metal salts selected from the following compounds as the alkali or inorganic electrolyte: silicates, carbonates and sulfates. Further, the composition may contain organic alkalis such as triethanolamine, diethanolamine, monoethanolamine, and triisopropanolamine.

MASKING AGENTS FOR FACTORS INHIBITING THE CELLULASE ACTIVITY

The cellulases are deactivated in some cases in the presence of heavy metal ions including copper, zinc, chromium, mercury, lead, manganese, or silver ions or their compounds. Various metal chelating agents and metal-precipitating agents are effective against these inhibitors. They include, for example, divalent metal ion sequestering agents as listed below with reference to optional additives as well as magnesium silicate and magnesium sulfate.

Cellubiose, glucose and gluconolactone can act as an inhibitor. It is preferred to avoid the co-presence of these saccharides with the cellulase if possible. In case the co-presence is unavoidable, it is necessary to avoid the direct contact of the saccharides with the cellulase by, for example, coating them.

Long chain fatty acid salts and cationic surfactants act as the inhibitors in some cases. However, the co-presence of these substances with the cellulase is allowable if the direct contact of them is prevented by some means such as tableting or coating.

The above-mentioned masking agents and methods may be employed, if necessary, in the present invention.

CELLULASE-ACTIVATORS

The activators vary depending on variety of the cellulases. In the presence of proteins, cobalt and its salts, magnesium and its salts, and calcium and its salts, potassium and its salts, sodium and its salts or monosaccharides such as mannose and xylose, the cellulases are activated and their deterging powers can be improved.

ANTIOXIDANTS

The antioxidants include, for example, tert-butylhydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4-hydroxyphenyl)cyclohexane.

SOLUBILIZERS

The solubilizers include, for example, lower alcohols such as ethanol, benzenesulfonate salts, lower alkylbenzenesulfonate salts such as p-toluenesulfonate salts, glycols such as propylene glycol, acetylbenzenesulfonate salts, acetamides, pyridinedicarboxylic acid amides, benzoate salts and urea.

The detergent composition of the present invention can be used in a broad pH range of about 6.5 to 10, preferably 6.5 to 8.

BUILDERS

Divalent Sequestering Agents

The composition may contain 0–50 wt-% of one or more builder components. For the purpose of this invention, the term builder (or builder salt) means a substance that increases the effectiveness of a surfactant or detergent by adding to its detergent power. Builders act as a source of alkalinity, as water softeners, and as sequestering and buffering agents. Such builder salt may be selected from the group consisting of alkali metal salts and alkanolamine salts of the following compounds: phosphates such as orthophosphate, pyrophosphate, tripolyphosphate, metaphosphate, hexametaphosphate and phytic acid; phosphonates such as ethane-1,1-diphosphonate, ethane-1,1,2-triphosphonate, ethane-1-hydroxy-1,1-diphosphonate and its derivatives. ethanehydroxy-1,1,2-triphosphonate, ethane-1,2-dicarboxy-1,2-diphosphonate and methanehydroxyphosphonate; phosphonocarboxylates such as 2-phosphonobutane-1,2-dicarboxylate, 1-phosphonobutane-2,3,4-tricarboxylate and α-methylphosphonosuccinate; salts of amino acids such as aspartic acid, glutamic acid and glycine; aminopolyacetates such as nitrilotriacetate, ethylenediaminetetraacetate, diethylenetriaminepentaacetate, iminodiacetate, glycol ether diamine tetraacetate, and hydroxyethyliminodiacetate; high molecular electrolytes such as polyacrylic acid, polyaconitic acid, polyitaconic acid, polycitraconic acid, polyfumaric acid, polymaleic acid, polymesaconic acid, poly-α-hydroxyacrylic acid, polyvinylphosphonic acid, sulfonated polymaleic acid, maleic anhydride/diisobutylene copolymer, maleic anhydride/styrene copolymer, maleic anhydride/methyl vinyl ether copolymer, maleic anhydride/ethylene copolymer, maleic anhydride/ethylene crosslinked copolymer, maleic anhydride/vinyl cetate copolymer, maleic anhydride/acrylonitrile copolymer, maleic anhydride/acrylic ester copolymer, maleic anhydride/butadiene copolymer, maleic anhydride/isoprene copolymer, poly-β-ketocarboxylic acid derived from maleic anhydride and carbon monoxide, itaconic acid/ethylene copolymer, itaconic acid/aconitic acid copolymer, itaconic acid/maleic acid copolymer, itaconic acid/acrylic acid copolymer, malonic acid/methylene copolymer, mesaconic acid/fumaric acid copolymer, ethylene glycol/ethylene terephthalate copolymer, vinylpyrrolidone/vinyl acetate copolymer, 1-butene-2,3,4-tricarboxylic acid/itaconic acid/acrylic acid copolymer, polyester polyaldehydocarboxylic acid containing quaternary ammonium group, cis-isomer of epoxysuccinic acid, poly[N,N-bis(carboxymethyl)acrylamide], poly(hydroxycarboxylic acid), starch/succinic acid or maleic acid or terephthalic acid ester, starch/phosphoric acid ester, dicarboxystarch, dicarboxymethylstarch, and cellulose/succinic acid ester; non-dissociating polymers such as polyethylene glycol, polyvinyl alcohol, polyvinyl pyrrolidone and cold water soluble, urethanated polyvinyl alcohol; and salts of dicarboxylic acids such as oxalic acid, malonic acid, succinic acid, glutaric acid, adipic acid, pimelic acid, suberic acid, azelaic acid and decane-1,10-dicarboxylic acid; salts of diglycolic acid, thiodiglycolic acid, oxalacetic acid, hydroxydisuccinic acid, carboxymethylhydroxysuccinic acid and carboxymethyltartronic acid; salts of hydroxycarboxylic acids such as glycolic acid, malic acid, hydroxypivalic acid, tartaric acid, citric acid, lactic acid, gluconic acid, mucic acid, glucuronic acid and dialdehydrostarch oxide; salts of itaconic acid, methylsuccinic acid, 3-methylglutaric acid, 2,2-dimethymalonic acid, maleic acid, fumaric acid, glutamic acid, 1,2,3-propanetricarboxylic acid, aconitic acid, 3-butene-1,2,3-tricarboxylic acid, butane-1,2,3,4-tetracarboxylic acid, ethanetetracarboxylic acid, ethenetetracarboxylic acid, n-alkenylaconitic acid, 1,2,3,4-cyclopentanetetracarboxylic acid, phthalic acid, trimesic acid, hemimellitic acid, pyromellitic acid, benzenehexacarboxylic acid, tetrahydrofuran-1,2,3,4-tetracarboxylic acid and tetrahydrofuran-2,2,5,5-tetracarboxylic acid; salts of sulfonated carboxylic acids such as sulfoitaconic acid, sulfotricarballylic acid, cysteic acid, sulfoacetic acid and sulfosuccinic acid; carboxymethylated sucrose, lactose and raffinose, carboxymethylated pentaerythritol, carboxymethylated gluconic acid, condensates of polyhydric alcohols or sugars with maleic anhydride or succinic anhydride, condensates of hydroxycarboxylic acids with maleic anhydride or succinic anhydride, and the like.

In somewhat greater detail, the clothing items can be contacted with an aqueous solution containing cellulase enzyme and a surfactant to promote the action of the cellulase for a sufficient time to produce local variations in color density in the surface of the fabric. The amount of solution used to treat the clothing items typically depends on the ratio of cellulase in the product and the dry weight of the clothing items to be washed. Typically the solutions used in the methods of the invention can contain a minimum of about 6,000 CMC units of cellulase per pound of clothes, preferably 6,500 to 75,000 units per pound, most preferably 12,000 to 60,000 units per pound to obtain the "stone-washed" look.

The treatment solutions used to contact the clothes can typically have the following ingredients.

TABLE 1

| | Aqueous Treating Compositions | | |
|---|---|---|---|
| Ingredient | Useful | Preferred | Most Preferred |
| Cellulase Enzyme* | >1,000 | 2,500–30,000 | 6,000–20,000 |
| Surfactant | 0–1,000 ppm | 10–900 ppm | 15–750 ppm |
| Water | Balance | Balance | Balance |

*Amounts in CMC $C_1$units per liter.

TABLE 2

| | Concentrate Compositions | | |
|---|---|---|---|
| Ingredient | Useful | Preferred | Most Preferred |
| Cellulase Enzyme | 1–90 wt % | 2–80 wt % | 5–75 wt % |
| Surfactant | 99–0 wt % | 98–5 wt % | 95–10 wt % |
| Solvent | Balance | Balance | Balance |

TABLE 3

| | Inorganic Solid Concentrate | | |
|---|---|---|---|
| Ingredient | Useful | Preferred | Most Preferred |
| Cellulase Enzyme | 25-90 wt % | 30-85 wt % | 35-80 wt % |
| Hydratable Inorganic Salt Buffer System | 20-60 wt % | 20-55 wt % | 25-50 wt % |
| Sequestrant | 0-25 wt % | 5-20 wt % | 7-15 wt % |
| Water of Hydration | Balance | Balance | Balance |

TABLE 4

| | Organic Solid Concentrate | | |
|---|---|---|---|
| Ingredient | Useful | Preferred | Most Preferred |
| Cellulase Enzyme | 25-90 wt % | 30-85 wt % | 35-80 wt % |
| Surfactant | 99-0 wt % | 98-5 wt % | 95-10 wt % |
| PEG* | 20-60 wt % | 20-55 wt % | 25-50 wt % |
| Sequestrant | 0-25 wt % | 5-20 wt % | 7-20 wt % |
| Buffer System | 0-5 wt % | 1-4 wt % | 1.5-3.5 wt % |

*PEG = polyethylene oxide (M.W. 1,000-9,000).

The liquid concentrate compositions of this invention can be formulated in commonly available industrial mixers. Typically a solution of the surfactant is prepared in the solvent and into the surfactant solution is added the cellulase enzyme sufficiently slowly to create a uniform enzyme dispersion in the solvent. The concentrates can be packaged in typical inert packaging such as glass, polyethylene or polypropylene, or PET. Care should be taken such that agitation does not significantly reduce the activity of the cellulase enzyme.

The inorganic solid concentrate compositions of this invention can be made by combining the cellulase enzyme with the inorganic (alkali metal or alkaline earth metal) hydratable carbonate, bicarbonate, silicate or sulfate in an aqueous slurry containing sufficient water to cause the hydration and solidification of the inorganic components. The slurries can be made at elevated temperatures to reduce viscosity and increase handleability. The inorganic slurry compositions can then be cast in molds and after solidification can be removed from the mold, packaged and sold. Alternatively, the materials can be cast in reusable or disposable containers, capped and sold. Such materials usually are manufactured in a 1 ounce to 10 pound size. Solid concentrates can be in the form of a pellet having a weight of 1 gram to 250 grams, preferably 2 grams to 150 grams. The large cast object can be about 300 grams to 5 kilograms, preferably 500 grams to 4 kilograms.

The organic enzyme concentrate compositions can typically be made by slurrying the enzyme material in a melted polymer matrix that can contain water for viscosity control purposes. Once a uniform dispersion of the enzyme, and other optional ingredients, are included in the organic polymer matrix, the materials can be introduced into molds or reusable or disposable containers, cooled, solidified and sold. Alternatively both the organic and inorganic solid concentrates can be made by combining the ingredients, and forming the compositions into pellets in commercially available pelletizing machines using either the temperature solidification, the hydration solidification mechanism, or a compression pelletizing machine using a binding agent well known in the art. All of the liquid and solid concentrate compositions of the invention can include additional ingredients that preserve or enhance the enzyme activity in the pumice-free stone wash processes of the invention.

The compositions of this invention are typically diluted in water in household, institutional, or industrial machines having a circular drum held in a horizontal or vertical mode in order to produce the "stone-washed" appearance without the use of pumice or other particulate abrasive. Most commonly the denim or other fabric clothing items are added to the machine according to the machine capacity per the manufacturer's instructions. Typically the clothes are added prior to introducing water into the drum but the clothes can be added to water in the machine or to the pre-diluted treatment composition. The clothing is contacted with the treatment composition and agitated in the machine for a sufficient period to ensure that the clothing has been fully wetted by the treatment composition and to ensure that the cellulase enzyme has had an opportunity to cleave cellulose in the fabric material. At this time if the treatment composition is to be reused, it is often drained from the tub and saved for recycle. If the treatment composition is not to be reused, it can remain on the clothing for as long as needed to produce color variation. Such treatment periods are greater than 5 minutes, greater than 30 minutes and up to 720 minutes, depending on amount of enzyme, during all or part of the mechanical machine action used to produce in the cellulase treated fabric the variations in color density. We believe that there is an interaction between the cellulase modified fabric and mechanical tumbling or action which removes cellulose from the fabric surface and the indigo dye to create a variation in color density from place to place on fabric panels and seams. Further, the action of the enzyme appears to cause puckering in the seams and a creation of a soft, wrinkled look in fabric panels.

The above specification provides a discussion of the compositions of the invention and methods of making and using the compositions in the "stone-washing" of fabric clothing items. The following Examples provide specific details with respect to the compositions and methods of the invention and include a best mode.

EXAMPLES I-III

Into a Milnor 35 lb. capacity washing machine was placed new blue denim jeans and into the machine was placed 25 gallons of 120° F. water containing an amylase enzyme desizing stripper composition. The contents of the machine was agitated for 9 minutes and the aqueous solution was dumped. Into the machine was placed 25 gallons of water at 120° F. containing an amount of cellulase enzyme (see Table 5 below) and 10 milliliters of a sour comprising an aqueous solution containing 23 wt-% $H_2SiF_6$ and 50 wt-% citric acid. The jeans were agitated in the celluzyme composition for 1 hour and the aqueous composition was dumped. The jeans were then rinsed in three successive hot water rinses at 120° F., 110° F., and a final rinse at 100° F. containing 5 milliliters of the sour product.

TABLE 6

| Visible Spectrophotometer Scan of Stone Washed Jeans and Product of Example II | | | |
|---|---|---|---|
| Wave Length | Stone Washed Jeans | Example II | Differences |
| 380 | 11.50 | 11.01 | −0.49 |
| 390 | 15.71 | 15.32 | −0.39 |
| 400 | 18.57 | 18.49 | −0.08 |
| 410 | 21.70 | 21.99 | 0.69 |

TABLE 6-continued

| Visible Spectrophotometer Scan of Stone Washed Jeans and Product of Example II | | | |
|---|---|---|---|
| Wave Length | Stone Washed Jeans | Example II | Differences |
| 420 | 23.01 | 24.22 | 1.20 |
| 430 | 22.96 | 24.24 | 1.28 |
| 440 | 22.19 | 23.53 | 1.34 |
| 450 | 21.31 | 22.62 | 1.31 |
| 460 | 20.38 | 21.64 | 1.26 |
| 470 | 19.43 | 20.63 | 1.20 |
| 480 | 18.60 | 19.71 | 1.10 |
| 490 | 17.91 | 18.92 | 1.01 |
| 500 | 17.18 | 18.08 | 0.90 |
| 510 | 16.35 | 17.13 | 0.77 |
| 520 | 15.40 | 16.06 | 0.66 |
| 530 | 14.40 | 14.92 | 0.52 |
| 540 | 13.47 | 13.88 | 0.41 |
| 550 | 12.77 | 13.08 | 0.31 |
| 560 | 12.32 | 12.60 | 0.28 |
| 570 | 11.94 | 12.15 | 0.21 |
| 580 | 11.42 | 11.59 | 0.17 |
| 590 | 10.85 | 10.97 | 0.12 |
| 600 | 10.35 | 10.39 | 0.04 |
| 610 | 9.95 | 9.94 | −0.01 |
| 620 | 9.60 | 9.56 | −0.04 |
| 630 | 9.15 | 9.07 | −0.08 |
| 640 | 8.75 | 8.64 | −0.11 |
| 650 | 8.44 | 8.30 | −0.14 |
| 660 | 8.35 | 8.21 | −0.14 |
| 670 | 8.66 | 8.58 | −0.08 |
| 680 | 9.70 | 9.73 | 0.03 |
| 690 | 11.83 | 12.12 | 0.29 |
| 700 | 15.83 | 16.60 | 0.77 |
| 710 | 22.62 | 23.99 | 1.37 |
| 720 | 32.13 | 33.84 | 1.71 |
| 730 | 42.55 | 43.96 | 1.41 |
| 740 | 51.26 | 51.92 | 0.65 |
| 750 | 57.04 | 57.03 | −0.01 |

TABLE 5

| Example | Concentrate Grams/L | CMCU*/L | CMCU*/LB | CMCU/Pair | Grams/Pair |
|---|---|---|---|---|---|
| I | 200 | 7,459 | 32,000 | 48,000 | 20 |
| II | 300 | 11,189 | 48,000 | 72,000 | 30 |
| III | 400 | 14,918 | 64,000 | 96,000 | 40 |

*Carboxymethyl cellulose units

DETAILED DISCUSSION OF THE DRAWINGS

FIG. 1 is a graphical representation of the data in the above table. The graph appears to be a single line consisting of dots and dashes, however the graph shows that the percent reflectance of the stone washed denims and the denims produced using the compositions and methods of this invention are virtually identical. The differences shown in column 4 of the above table indicate that at certain wavelengths minor differences occur, however the curves are virtually superimposable.

I claim:

1. A method of forming, in unsewn dyed denim fabric or in a newly manufactured garment made of a dyed denim fabric, localized areas of variation in color density through the removal of dye that provide a stone washed appearance, which method consists essentially of:

(1) contacting the unsewn fabric or garment with an aqueous composition consisting essentially of:
(a) a major proportion of water;
(b) at least about 2500 CMC units of a cellulase enzyme composition per liter of aqueous composition; and (2) subjecting the unsewn fabric or garment to mechanical action for a sufficient time for said cellulase enzyme to produce variations in color substantially the same as the stone washed appearance produced by pumice stone processing.

2. The method of claim 1, wherein the mechanical action is a machine agitation.

3. The method of claim 1 wherein after the fabric or garment is contacted with the aqueous composition, but before mechanical action, the aqueous composition is removed from contact with the fabric or garment.

4. The method of claim 1 wherein the unsewn fabric or garment is contacted with the aqueous composition for at least five minutes.

5. The method of claim 1 wherein the unsewn fabric or garment is subjected to mechanical agitation for 30 to 720 minutes.

6. The method of claim 1 wherein the cellulase is a fungal cellulase.

7. The method of claim 1 wherein the unsewn fabric or fabric of the garment is indigo dyed denim.

8. The method of claim 1 wherein the garment is indigo dyed denim pants.

9. The method of claim 1 wherein the garment is an indigo dyed denim jacket.

10. The method of claim 1 wherein the aqueous composition additionally consists essentially of an electrolyte.

11. The method of claim 1 wherein the aqueous composition additionally consists essentially of a builder salt.

12. The method of claim 1 wherein the aqueous composition additionally consists essentially of a buffer system capable of maintaining the pH near the pH of optimal activity for the enzyme.

13. A method of forming, in unsew indigo dyed denim fabric or a newly manufactured garment made of an indigo dyed denim fabric, localized areas of variation in color density through the removal of indigo dye that provide a stone washed appearance, which method consists essentially of:

(1) contacting the unsewn fabric or the garment with an aqueous composition consisting essentially of:
(a) a major proportion of water;
(b) at least about 2500 CMC units of a cellulase enzyme composition per liter of aqueous composition;
(c) about 1 to 50 wt-% of an electrolyte; and
(d) about 20 to 60 wt-% of a buffer capable of maintaining the pH at the pH of optimal activity for the cellulase enzyme; and (2) subjecting the unsewn fabric or garment to mechanical action for a sufficient period of time for said cellulase enzyme to produce variations in color density substantially the same as the stone washed appearance produced by pumice stone processing.

14. The method of claim 13 wherein the cellulase is a fungal cellulase.

15. The method of claim 13 wherein the buffer is a phosphate buffer.

16. The method of claim 13 wherein the unsewn fabric or garment is contacted with the aqueous composition for at least five minutes.

17. The method of claim 13 wherein the unsewn fabric or garment is subjected to mechanical agitation for 30 to 720 minutes.

18. A method of claim 13, wherein the mechanical action is a machine agitation.

* * * * *

US004912056B1

REEXAMINATION CERTIFICATE (3165th)

United States Patent [19]

[11] B1 4,912,056

Olson

[45] Certificate Issued *Apr. 1, 1997

[54] TREATMENT OF DENIM WITH CELLULASE TO PRODUCE A STONE WASHED APPEARANCE

[75] Inventor: Lynne A. Olson, Mendota Heights, Minn.

[73] Assignee: IVAX Industries, Inc., Horsham, Pa.

Reexamination Request:
No. 90/003,775, Apr. 3, 1995

Reexamination Certificate for:

| | |
|---|---|
| Patent No.: | **4,912,056** |
| Issued: | **Mar. 27, 1990** |
| Appl. No.: | **283,563** |
| Filed: | **Dec. 8, 1988** |

[ * ] Notice: The portion of the term of this patent subsequent to May 23, 2006, has been disclaimed.

Related U.S. Application Data

[62] Division of Ser. No. 96,953, Sep. 15, 1987, Pat. No. 4,832, 864.

[51] Int. Cl.[6] .............................. D06M 16/00; C12N 9/96; C12N 9/42

[52] U.S. Cl. ...................... 435/263; 8/116.1; 252/174.12; 252/DIG. 12; 435/188; 435/209; 435/264

[58] Field of Search .................................... 435/188, 209, 435/263; 8/264, 102, 116.1; 252/174.12, DIG. 12

[56] References Cited

U.S. PATENT DOCUMENTS

| | | | |
|---|---|---|---|
| 4,381,247 | 4/1983 | Nakagawa et al. | 252/95 |
| 4,388,077 | 6/1983 | Ruck | 8/138 |
| 4,435,307 | 3/1984 | Barbesgaard et al. | 252/174 |
| 4,443,355 | 4/1984 | Murata et al. | 252/174.12 |
| 4,479,881 | 10/1984 | Tai | 252/8.8 |
| 4,661,289 | 4/1987 | Parslow et al. | 252/547 |

FOREIGN PATENT DOCUMENTS

| | | |
|---|---|---|
| 177165 | 4/1986 | European Pat. Off. . |
| 0220016 | 7/1986 | European Pat. Off. . |
| 252317 | 1/1988 | European Pat. Off. . |
| 1368599 | 9/1970 | United Kingdom . |
| 2095275 | 9/1982 | United Kingdom . |
| 2094826 | 9/1982 | United Kingdom . |
| 2136029 | 9/1984 | United Kingdom . |

OTHER PUBLICATIONS

Matti Leisola & Matti Linko, *Determination of the Solubilizing Activity of a Cellulase Complex with Dyed Substrates*, Analytical Biochemistry 70, 592–599 (1976).

Novo Enzymes Detergent Cellulase—SP 227 Brochure, published Apr. 1987.

Novo Celluzyme brochure.

Amano Cellulase AP brochure.

Merck Index, p. 210, 8th edition, 1968.

Wall Street Journal, May 29, 1987, pp. 1,9.

*Primary Examiner*—David M. Naff

[57] ABSTRACT

Denim having a stone washed appearance is produced without stones by treating with a cellulase enzyme. Unsewn dyed denim fabric or a newly manufactured garment made of dyed denim fabric is contacted with an aqueous composition containing at least about 2500 CMCS units of cellulase per liter, and subjected to mechanical action. Preferably, the aqueous composition provides at least about 6000 CMC units of cellulase per pound of unsewn fabric or garment. The aqueous may also contain an electrolyte, a buffer, a builder salt a cellulase activator, an antioxidant and a solubilizer.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–18 is confirmed.

* * * * *